United States Patent [19]

Gehring et al.

[11] Patent Number: 4,791,212

[45] Date of Patent: Dec. 13, 1988

[54] 4-ALKENYLAMINOCARBONYL- AND 4-ALKINYLAMINOCARBONYL-1-PHENYL-5-PYRAZOLAMINES

[75] Inventors: Reinhold Gehring, Wuppertal; Erich Klauke, Odenthal; Otto Schallner, Monheim; Jörg Stetter, Wuppertal; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 947,667

[22] Filed: Dec. 30, 1986

Related U.S. Application Data

[62] Division of Ser. No. 659,731, Oct. 11, 1984, Pat. No. 4,668,280.

[30] Foreign Application Priority Data

Oct. 15, 1983 [DE] Fed. Rep. of Germany ....... 3337543
Jun. 6, 1984 [DE] Fed. Rep. of Germany ....... 3420985

[51] Int. Cl.$^4$ ............................................. C07D 231/38
[52] U.S. Cl. ..................................................... 548/362
[58] Field of Search ............................. 548/362; 71/92

[56] References Cited

U.S. PATENT DOCUMENTS

| | | | |
|---|---|---|---|
| 4,420,324 | 12/1983 | Eicken et al. ........................ | 548/362 |
| 4,459,150 | 7/1984 | Hatton et al. ........................ | 548/362 |
| 4,472,192 | 9/1984 | Eicken et al. ........................ | 548/362 |
| 4,496,390 | 1/1985 | Hatton et al. ........................ | 71/92 |

FOREIGN PATENT DOCUMENTS 2070604 9/1981 United Kingdom ................ 548/362

*Primary Examiner*—Mary C. Lee
*Assistant Examiner*—Kurt G. Briscoe
*Attorney, Agent, or Firm*—Sprung Horn Kramer & Woods

[57] ABSTRACT

A 5-aminopyrazole of the formula

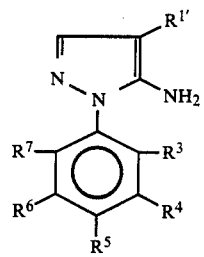

in which
 $R^1$ represents alkoxycarbonyl, alkenyloxycarbonyl, alkinyloxycarbonyl, alkenylaminocarbonyl or alkinylaminocarbonyl and
 $R^3$, $R^4$, $R^5$, $R^6$ and $R^7$, which are identical or different, represent hydrogen, halogen, cyano, nitro, alkyl, alkoxy, alkylsulphonyl, alkoxycarbonyl or a radical —(X)n—$R^8$
wherein
 X represents oxygen, sulphur, sulphinyl or sulphonyl,
 n represents 0 or 1 and
 $R^8$ represents halogenoalkyl, with the proviso that at least one of the radicals $R^3$, $R^4$, $R^5$, $R^6$ and $R^7$ represents a radical —(X)$_n$—$R^8$, but $R^1$ does not represent cyano if $R^1$ represents trifluoromethyl.

These compounds are intermediates useful in the preparation of herbicidally active substituted 5-acylamino-1-phenylpyrazoles.

2 Claims, No Drawings

4-ALKENYLAMINOCARBONYL- AND 4-ALKINYLAMINOCARBONYL-1-PHENYL-5-PYRAZOLAMINES

This is a division of application Ser. No. 659,731, filed Oct. 11, 1984, now U.S. Pat. No. 4,668,280.

The invention relates to new substituted 5-acylamino-1-phenylpyrazoles, a process for their preparation and their use as herbicides.

It has already been disclosed that certain substituted 5-acylamino-1-phenylpyrazoles, such as, for example, 4-cyano-5-propionamido-1-(2,4,6-trichlorophenyl)-pyrazole, have herbicidal properties (compare, for example, DE-OS (German published specification) No. 3,226,513).

However, the herbicidal action of these known compounds against weeds and their tolerance towards important crop plants is not always completely satisfactory in all cases.

New substituted 5-acylamino-1-phenylpyrazoles of the general formula (I)

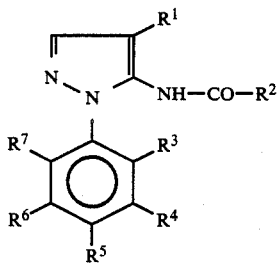

in which $R^1$ represents cyano, alkoxycarbonyl, alkenyloxycarbonyl, alkinyloxycarbonyl, aminocarbonyl, alkylaminocarbonyl, alkenylaminocarbonyl or alkinylaminocarbonyl, $R^2$ represents hydrogen, alkyl, alkenyl, alkinyl, optionally substituted cycloalkyl, alkoxyalkyl, alkylthioalkyl, halogenoalkyl or optionally substituted aryl and $R^3$, $R^4$, $R^5$, $R^6$ and $R^7$, which are identical or different, represent hydrogen, halogen, cyano, nitro, alkyl, alkoxy, alkylsulphonyl, alkoxycarbonyl or a radical $-(X)_n-R^8$, wherein X represents oxygen, sulphur, sulphinyl or sulphonyl, n represents 0 or 1 and $R^8$ represents halogenoalkyl, with the proviso that at least one of the radicals $R^3$, $R^4$, $R^5$, $R^6$ or $R^7$ represents a radical $-(X)_n-R^8$, but $R^1$ does not represent cyano if $R^5$ represents trifluoromethyl, have been found.

It has furthermore been found that the new substituted 5-acylamino-1-phenylpyrazoles of the general formula (I) are obtained when 5-amino-pyrazoles of the formula (II)

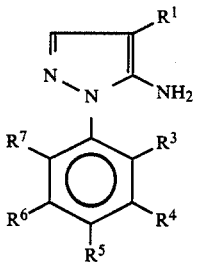

in which $R^1$, $R^3$, $R^4$, $R^5$, $R^6$ and $R^7$ have the above-mentioned meaning, are reacted with acylating agents of the formula (III)

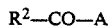

$$R^2-CO-A \qquad (III)$$

in which $R^2$ has the abovementioned meaning and

A represents an activating leaving group, if appropriate in the presence of a diluent and if appropriate in the presence of an acid-binding agent.

Finally, it has been found that the new substituted 5-acylamino-1-phenylpyrazoles of the formula (I) have herbicidal properties, in particular also selective herbicidal properties.

Surprisingly, the new substituted 5-acylamino-1-phenylpyrazoles of the formula (I) have a better herbicidal activity against harmful plants, coupled with a better tolerance towards important useful plants, than, for example, 4-cyano-5-propionamido-1-(2,4,6-trichlorophenyl)-pyrazole, which is known from the prior art and is a closely related compound chemically and from the point of view of its action.

Formula (I) provides a general definition of the new substituted 5-acylamino-1-phenylpyrazoles. Preferred compounds of the formula (I) are those in which $R^1$ represents cyano or aminocarbonyl, or represents in each case straight-chain or branched alkoxycarbonyl, alkenyloxycarbonyl, alkinyloxycarbonyl, alkylaminocarbonyl, alkenylaminocarbonyl or alkinylaminocarbonyl with in each case up to 4 carbon atoms in the individual alkyl parts, $R^2$ represents hydrogen, or represents in each case straight-chain or branched alkyl, alkenyl or alkinyl with up to 6 carbon atoms, or represents cycloalkyl which has 3 to 7 carbon atoms and is optionally monosubstituted or polysubstituted by identical or different halogen atoms, or represents in each case straight-chain or branched alkoxyalkyl or alkylthioalkyl with in each case up to 4 carbon atoms in the individual alkyl parts, or represents straight-chain or branched halogenoalkyl with up to 6 carbon atoms and up to 9 identical or different halogen atoms, or represents phenyl which is optionally monosubstituted or polysubstituted by identical or different substituents, possible substituents being: halogen, cyano, nitro and in each case straight-chain or branched alkyl, alkoxy, alkylthio and alkoxycarbonyl with in each case up to 4 carbon atoms in the individual alkyl parts, and $R^3$, $R^4$, $R^5$, $R^6$ and $R^7$ independently of one another represent hydrogen, fluorine, chlorine, bromine, iodine, cyano, nitro, in each case straight-chain or branched alkyl, alkoxy, alkylsulphonyl or alkoxycarbonyl with up to 4 carbon atoms in the particular alkyl parts, or a radical —(X)$_n$—R$^8$,
wherein X represents oxygen, sulphur, sulphinyl or sulphonyl, n represents 0 or 1 and R$^8$ represents straight-chain or branched halogenoalkyl with up to 4 carbon atoms and up to 9 identical or different halogen atoms, with the proviso that at least one of the radicals R$^3$, R$^4$, R$^5$, R$^6$ or R$^7$ represents a radical —(X)$_n$—R$^8$, and R$^1$ does not represent cyano if R$^5$ represents trifluoromethyl.

Particularly preferred compounds of the formula (I) are those in which

R$^1$ represents cyano, methoxycarbonyl, ethoxycarbonyl, allyloxycarbonyl, propargyloxycarbonyl, aminocarbonyl, methylaminocarbonyl, dimethylaminocarbonyl, ethylaminocarbonyl, diethylaminocarbonyl, diallylaminocarbonyl or dipropargylaminocarbonyl, R$^2$ represents hydrogen, methyl, ethyl, n- or i-propyl, n-, i-, s- or t-butyl, cyclopropyl, 2,2-dichlorocyclopropyl, 2,2-dichloro-1-methylcyclopropyl, methylthiomethyl, cyclopentyl, cyclohexyl, ethoxymethyl, methoxymethyl, methoxyethyl, ethoxyethyl, chloromethyl, dichloromethyl, trichloromethyl, trifluoromethyl, dichlorofluoromethyl, difluorochloromethyl or pentafluoroethyl, or represents phenyl which is mono-, di- or tri-substituted by identical or different radicals from the group comprising fluorine, chlorine, bromine, NO$_2$, methyl and methoxy, and R$^3$, R$^4$, R$^5$, R$^6$ and R$^7$ independently of one another represent hydrogen, fluorine, chlorine, bromine, cyano, nitro, methyl, ethyl, n- or i-propyl, methoxy, ethoxy, methylsulphonyl, methoxycarbonyl or ethoxycarbonyl, or a radical —(X)$_n$—R$^8$,
wherein X represents oxygen, sulphur, sulphinyl or sulphonyl, n represents 0 or 1 and R$^8$ represents trifluoromethyl, trichloromethyl, dichlorofluoromethyl, difluorochloromethyl, dichloromethyl, chloromethyl, difluoromethyl, pentafluoroethyl, tetrafluoroethyl, trifluorochloroethyl, trifluoroethyl, difluorodichloroethyl, trifluorodichloroethyl or pentachloroethyl, with the proviso that at least one of the radicals R$^3$, R$^4$, R$^5$, R$^6$ or R$^7$ represents a radical —(X)$_n$—R$^8$, and R$^1$ does not represent cyano if R$^5$ represents trifluoromethyl.

The following compounds of the general formula (I) may be mentioned specifically, in addition to the compounds mentioned in the preparation examples:

TABLE 1

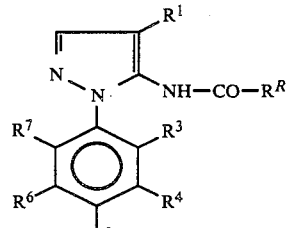

| R$^1$ | R$^2$ | R$^3$ | R$^4$ | R$^5$ | R$^6$ | R$^7$ |
|---|---|---|---|---|---|---|
| CN | H | F | H | OCF$_3$ | H | H |
| CN | H | F | H | OCF$_3$ | H | F |
| CN | H | F | F | OCF$_3$ | F | F |
| CN | H | Cl | H | OCF$_3$ | H | H |
| CN | H | Cl | H | OCF$_3$ | H | Cl |
| CN | H | Cl | Cl | OCF$_3$ | H | H |

TABLE 1-continued

| R$^1$ | R$^2$ | R$^3$ | R$^4$ | R$^5$ | R$^6$ | R$^7$ |
|---|---|---|---|---|---|---|
| CN | H | Cl | H | OCF$_3$ | H | F |
| CN | H | Br | H | OCF$_3$ | H | H |
| CN | H | Br | H | OCF$_3$ | H | Br |
| CN | CH$_3$ | F | H | OCF$_3$ | H | H |
| CN | CH$_3$ | F | H | OCF$_3$ | H | F |
| CN | CH$_3$ | F | F | OCF$_3$ | F | F |
| CN | CH$_3$ | Cl | H | OCF$_3$ | H | H |
| CN | CH$_3$ | Cl | H | OCF$_3$ | H | Cl |
| CN | CH$_3$ | Cl | Cl | OCF$_3$ | H | H |
| CN | CH$_3$ | Cl | H | OCF$_3$ | H | F |
| CN | CH$_3$ | Br | H | OCF$_3$ | H | H |
| CN | CH$_3$ | Br | H | OCF$_3$ | H | Br |
| CN | C$_2$H$_5$ | F | H | OCF$_3$ | H | H |
| CN | C$_2$H$_5$ | F | H | OCF$_3$ | H | F |
| CN | C$_2$H$_5$ | F | F | OCF$_3$ | F | F |
| CN | C$_2$H$_5$ | Cl | H | OCF$_3$ | H | H |
| CN | C$_2$H$_5$ | Cl | H | OCF$_3$ | H | Cl |
| CN | C$_2$H$_5$ | Cl | Cl | OCF$_3$ | H | H |
| CN | C$_2$H$_5$ | Cl | H | OCF$_3$ | H | F |
| CN | C$_2$H$_5$ | Br | H | OCF$_3$ | H | H |
| CN | C$_2$H$_5$ | Br | H | OCF$_3$ | H | Br |
| CN | ▷◁H (cyclopropyl) | F | H | OCF$_3$ | H | H |
| CN | ▷◁H | F | H | OCF$_3$ | H | F |
| CN | ▷◁H | F | F | OCF$_3$ | F | F |
| CN | ▷◁H | Cl | H | OCF$_3$ | H | H |
| CN | ▷◁H | Cl | H | —OCF$_3$ | H | Cl |
| CN | ▷◁H | Cl | Cl | —OCF$_3$ | H | H |
| CN | ▷◁H | Cl | H | —OCF$_3$ | H | F |
| CN | ▷◁H | Br | H | —OCF$_3$ | H | H |
| CN | ▷◁H | Br | H | —OCF$_3$ | H | Br |
| CN | CH$_3$ | Cl | H | —S—CH$_2$CF$_3$ | H | H |
| CN | CH$_3$ | Cl | H | —S—CH$_2$CF$_3$ | H | Cl |
| CN | CH$_3$ | Br | H | —S—CH$_2$CF$_3$ | H | H |
| CN | CH$_3$ | Br | H | —S—CH$_2$CF$_3$ | H | Br |
| CN | CH$_3$ | Cl | Cl | —S—CH$_2$CF$_3$ | H | H |
| CN | C$_2$H$_5$ | Cl | H | —S—CH$_2$CF$_3$ | H | H |
| CN | C$_2$H$_5$ | Cl | H | —S—CH$_2$CF$_3$ | H | Cl |
| CN | C$_2$H$_5$ | Br | H | —S—CH$_2$CF$_3$ | H | H |
| CN | C$_2$H$_5$ | Br | H | —S—CH$_2$CF$_3$ | H | Br |
| CN | C$_2$H$_5$ | Cl | Cl | —S—CH$_2$CF$_3$ | H | H |

TABLE 1-continued

Structure (I):

Pyrazole bearing R¹ at 4-position, NH-CO-R^R at 5-position, and phenyl N-substituent with R³, R⁴, R⁵, R⁶, R⁷ substituents.

| R¹ | R² | R³ | R⁴ | R⁵ | R⁶ | R⁷ |
|---|---|---|---|---|---|---|
| CN | cyclopropyl | Cl | H | —S—CH₂CF₃ | H | H |
| CN | cyclopropyl | Cl | H | —S—CH₂CF₃ | H | Cl |
| CN | cyclopropyl | Br | H | —S—CH₂CF₃ | H | H |
| CN | cyclopropyl | Br | H | —S—CH₂CF₃ | H | Br |
| CN | cyclopropyl | Cl | Cl | —S—CH₂CF₃ | H | H |
| CN | CH₃OCH₂— | Cl | H | —S—CH₂CF₃ | H | H |
| CN | CH₃OCH₂— | Cl | H | —S—CH₂CF₃ | H | Cl |
| CN | CH₃OCH₂— | Br | H | —S—CH₂CF₃ | H | H |
| CN | CH₃OCH₂— | Br | H | —S—CH₂CF₃ | H | Br |
| CN | CH₃OCH₂— | Cl | Cl | —S—CH₂CF₃ | H | H |
| CN | CH₃ | Cl | H | —O—CH₂CF₃ | H | H |
| CN | CH₃ | Cl | H | —O—CH₂CF₃ | H | Cl |
| CN | CH₃ | Br | H | —O—CH₂CF₃ | H | H |
| CN | CH₃ | Br | H | —O—CH₂CF₃ | H | Br |
| CN | C₂H₅ | Cl | H | —O—CH₂CF₃ | H | H |
| CN | C₂H₅ | Cl | H | —O—CH₂CF₃ | H | Cl |
| CN | C₂H₅ | Br | H | —O—CH₂CF₃ | H | H |
| CN | C₂H₅ | Br | H | —O—CH₂CF₃ | H | Br |
| CN | cyclopropyl | Cl | H | —O—CH₂CF₃ | H | H |
| CN | cyclopropyl | Cl | H | —O—CH₂CF₃ | H | Cl |
| CN | cyclopropyl | Br | H | —O—CH₂CF₃ | H | H |
| CN | cyclopropyl | Br | H | —O—CH₂CF₃ | H | Br |
| CN | CH₃OCH₂— | Cl | H | —O—CH₂CF₃ | H | H |
| CN | CH₃OCH₂— | Cl | H | —O—CH₂CF₃ | H | Cl |
| CN | CH₃OCH₂— | Br | H | —O—CH₂CF₃ | H | H |
| CN | CH₃OCH₂— | Br | H | —O—CH₂CF₃ | H | Br |
| CN | CH₃ | SCF₃ | H | Cl | H | H |
| CN | C₂H₅ | SCF₃ | H | Cl | H | H |
| CN | CH₃ | SCF₃ | H | Cl | H | Cl |
| CN | C₂H₅ | SCF₃ | H | Cl | H | Cl |
| CN | H | F | H | SCF₃ | H | H |
| CN | H | F | H | SCF₃ | H | F |
| CN | H | F | F | SCF₃ | F | F |
| CN | H | Cl | H | SCF₃ | H | H |
| CN | H | Cl | H | SCF₃ | H | Cl |
| CN | H | Cl | Cl | SCF₃ | H | H |
| CN | H | Cl | H | SCF₃ | H | F |
| CN | H | Br | H | SCF₃ | H | H |
| CN | H | Br | H | SCF₃ | H | Br |
| CN | CH₃ | F | H | SCF₃ | H | H |
| CN | CH₃ | F | H | SCF₃ | H | F |
| CN | CH₃ | F | F | SCF₃ | F | F |
| CN | CH₃ | Cl | H | SCF₃ | H | H |
| CN | CH₃ | Cl | H | SCF₃ | H | Cl |
| CN | CH₃ | Cl | Cl | SCF₃ | H | H |
| CN | CH₃ | Cl | H | SCF₃ | H | F |
| CN | CH₃ | Br | H | SCF₃ | H | H |
| CN | CH₃ | Br | H | SCF₃ | H | Br |
| CN | C₂H₅ | F | H | SCF₃ | H | H |
| CN | C₂H₅ | F | H | SCF₃ | H | F |
| CN | C₂H₅ | F | H | SCF₃ | F | F |
| CN | C₂H₅ | Cl | H | SCF₃ | H | H |
| CN | C₂H₅ | Cl | H | SCF₃ | H | Cl |
| CN | C₂H₅ | Cl | H | SCF₃ | H | F |
| CN | C₂H₅ | Br | H | SCF₃ | H | H |
| CN | cyclopropyl | F | H | SCF₃ | H | H |
| CN | cyclopropyl | F | H | SCF₃ | H | F |
| CN | cyclopropyl | F | F | SCF₃ | F | F |
| CN | cyclopropyl | Cl | H | SCF₃ | H | H |
| CN | cyclopropyl | Cl | H | SCF₃ | H | Cl |
| CN | cyclopropyl | Cl | Cl | SCF₃ | H | H |
| CN | cyclopropyl | Cl | H | SCF₃ | H | F |
| CN | cyclopropyl | Br | H | SCF₃ | H | H |
| CN | cyclopropyl | Br | H | SCF₃ | H | Br |
| CN | H | CF₃ | H | —SO₂CH₃ | H | H |
| CN | H | CF₃ | H | —SO₂CH₃ | H | H |
| CN | H | CF₃ | H | —SCF₃ | H | H |
| CN | H | OCF₃ | H | —CF₃ | H | H |
| CN | H | OCF₃ | H | —OCF₃ | H | H |
| CN | CH₃ | CF₃ | H | —SO₂CH₃ | H | H |
| CN | CH₃ | CF₃ | H | —SO₂CH₃ | H | H |
| CN | CH₃ | CF₃ | H | —SCF₃ | H | H |
| CN | CH₃ | OCF₃ | H | —OCF₃ | H | H |
| CN | CH₃ | OCF₃ | H | —CF₃ | H | H |
| CN | C₂H₅ | CF₃ | H | —SO₂CH₃ | H | H |
| CN | C₂H₅ | CF₃ | H | —SO₂CH₃ | H | H |
| CN | C₂H₅ | CF₃ | H | —SCF₃ | H | H |
| CN | C₂H₅ | OCF₃ | H | —OCF₃ | H | H |
| CN | C₂H₅ | OCF₃ | H | —CF₃ | H | H |

TABLE 1-continued

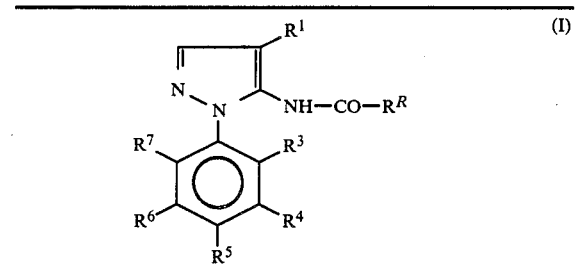
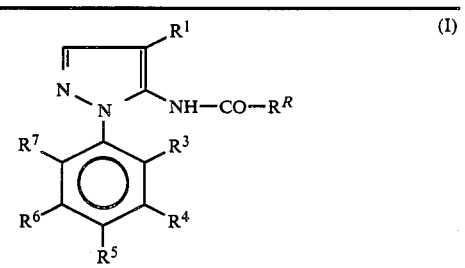

| R¹ | R² | R³ | R⁴ | R⁵ | R⁶ | R⁷ |
|---|---|---|---|---|---|---|
| CN | cyclopropyl-H | $CF_3$ | H | $-SO_2CH_3$ | H | H |
| CN | cyclopropyl-H | $CF_3$ | H | $-SO_2CH_3$ | H | H |
| CN | cyclopropyl-H | $CF_3$ | H | $-SCF_3$ | H | H |
| CN | cyclopropyl-H | $OCF_3$ | H | $-OCF_3$ | H | H |
| CN | cyclopropyl-H | $OCF_3$ | H | $-CF_3$ | H | H |
| CN | H | Cl | H | $-SCHF_2$ | H | H |
| CN | H | Cl | H | $-SCHF_2$ | H | Cl |
| CN | H | Br | H | $-SCHF_2$ | H | H |
| CN | H | Br | H | $-SCHF_2$ | H | Br |
| CN | $CH_3$ | Cl | H | $-SCHF_2$ | H | H |
| CN | $CH_3$ | Cl | H | $-SCHF_2$ | H | Cl |
| CN | $CH_3$ | Br | H | $-SCHF_2$ | H | H |
| CN | $CH_3$ | Br | H | $-SCHF_2$ | H | Br |
| CN | $C_2H_5$ | Cl | H | $-SCHF_2$ | H | H |
| CN | $C_2H_5$ | Cl | H | $-SCHF_2$ | H | Cl |
| CN | $C_2H_5$ | Br | H | $-SCHF_2$ | H | H |
| CN | $C_2H_5$ | Br | H | $-SCHF_2$ | H | Br |
| CN | cyclopropyl-H | Cl | H | $-SCHF_2$ | H | H |
| CN | cyclopropyl-H | Cl | H | $-SCHF_2$ | H | Cl |
| CN | cyclopropyl-H | Br | H | $-SCHF_2$ | H | H |
| CN | cyclopropyl-H | Br | H | $-SCHF_2$ | H | Br |
| CN | H | Cl | H | $-SCF_2CHF_2$ | H | H |
| CN | H | Cl | H | $-SCF_2CHF_2$ | H | Cl |
| CN | H | Br | H | $-SCF_2CHF_2$ | H | H |
| CN | H | Br | H | $-S-CF_2CHF_2$ | H | Br |
| CN | $CH_3$ | Cl | H | $-SCF_2CHF_2$ | H | H |
| CN | $CH_3$ | Cl | H | $-SCF_2CHF_2$ | H | Cl |
| CN | $CH_3$ | Br | H | $-SCF_2CHF_2$ | H | H |
| CN | $CH_3$ | Br | H | $-SCF_2CHF_2$ | H | Br |
| CN | $C_2H_5$ | Cl | H | $-SCF_2CHF_2$ | H | H |
| CN | $C_2H_5$ | Cl | H | $-S-CF_2CHF_2$ | H | Cl |
| CN | $C_2H_5$ | Br | H | $-SCF_2CHF_2$ | H | H |
| CN | $C_2H_5$ | Br | H | $-SCF_2CHF_2$ | H | Br |
| CN | cyclopropyl-H | Cl | H | $-SCF_2CHF_2$ | H | H |
| CN | cyclopropyl-H | Cl | H | $-SCF_2CHF_2$ | H | Cl |
| CN | cyclopropyl-H | Br | H | $-SCF_2CHF_2$ | H | H |
| CN | cyclopropyl-H | Br | H | $-SCF_2CHF_2$ | H | Br |
| CN | H | Cl | H | $-SCF_2CHFCl$ | H | H |
| CN | H | Cl | H | $-SCF_2CHFCl$ | H | Cl |
| CN | H | Br | H | $-SCF_2CHFCl$ | H | H |
| CN | H | Br | H | $-SCF_2CHFCl$ | H | Br |
| CN | $CH_3$ | Cl | H | $-SCF_2CHFCl$ | H | H |
| CN | $CH_3$ | Cl | H | $-SCF_2CHFCl$ | H | Cl |
| CN | $CH_3$ | Br | H | $-SCF_2CHFCl$ | H | H |
| CN | $CH_3$ | Br | H | $-SCF_2CHFCL$ | H | Br |
| CN | $C_2H_5$ | Cl | H | $-SCF_2CHFCl$ | H | H |
| CN | $C_2H_5$ | Cl | H | $-SCF_2CHFCl$ | H | Cl |
| CN | $C_2H_5$ | Br | H | $-SCF_2CHFCl$ | H | H |
| CN | $C_2H_5$ | Br | H | $-SCF_2CHFCl$ | H | Br |
| CN | cyclopropyl-H | Cl | H | $-SCF_2CHFCl$ | H | H |
| CN | cyclopropyl-H | Cl | H | $-SCF_2CHFCl$ | H | Cl |
| CN | cyclopropyl-H | Br | H | $-SCF_2CHFCl$ | H | H |
| CN | cyclopropyl-H | Br | H | $-SCF_2CHFCl$ | H | Br |
| CN | $ClCH_2-$ | Cl | H | $-SCF_3$ | H | H |
| CN | $ClCH_2-$ | Cl | H | $-OCF_3$ | H | Cl |
| CN | $ClCH_2-$ | Br | H | $-OCF_3$ | H | H |
| CN | $ClCH_2-$ | Br | H | $-OCF_3$ | H | Br |
| CN | $CH_3OCH_2-$ | Cl | H | $-OCF_3$ | H | H |
| CN | $CH_3OCH_2-$ | Cl | H | $-OCF_3$ | H | Cl |
| CN | $ClCH_2-$ | Cl | H | $-SCF_3$ | H | H |
| CN | $ClCH_2-$ | Cl | H | $-SCF_3$ | H | Cl |
| CN | $ClCH_2-$ | Br | H | $-SCF_3$ | H | H |
| CN | H | Cl | H | $-SOCF_3$ | H | H |
| CN | H | Cl | H | $-SOCF_3$ | H | Cl |
| CN | H | Br | H | $-SOCF_3$ | H | Br |
| CN | H | Br | H | $-SOCF_3$ | H | H |
| CN | H | $CF_3$ | H | $-SOCF_3$ | H | H |
| CN | H | $CF_3$ | H | $-SOCF_3$ | H | Cl |
| CN | $CH_3$ | Cl | H | $-SOCF_3$ | H | H |
| CN | $CH_3$ | Cl | H | $-SOCF_3$ | H | Cl |
| CN | $CH_3$ | Br | H | $-SOCF_3$ | H | Br |
| CN | $CH_3$ | Br | H | $-SOCF_3$ | H | H |
| CN | $CH_3$ | $CF_3$ | H | $-SOCF_3$ | H | H |
| CN | $CH_3$ | $CF_3$ | H | $-SOCF_3$ | H | Cl |
| CN | $C_2H_5$ | Cl | H | $-SOCF_3$ | H | H |
| CN | $C_2H_5$ | Cl | H | $-SOCF_3$ | H | Cl |
| CN | $C_2H_5$ | Br | H | $-SOCF_3$ | H | Br |
| CN | $C_2H_5$ | Br | H | $-SOCF_3$ | H | H |
| CN | $C_2H_5$ | $CF_3$ | H | $-SOCF_3$ | H | H |
| CN | $C_2H_5$ | $CF_3$ | H | $-SOCF_3$ | H | Cl |

TABLE 1-continued

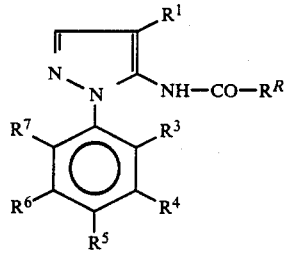 (I)

| R¹ | R² | R³ | R⁴ | R⁵ | R⁶ | R⁷ |
|---|---|---|---|---|---|---|
| CN | cyclopropyl | Cl | H | —SOCF₃ | H | H |
| CN | cyclopropyl | Cl | H | —SOCF₃ | H | Cl |
| CN | cyclopropyl | Br | H | —SOCF₃ | H | Br |
| CN | cyclopropyl | Br | H | —SOCF₃ | H | H |
| CN | cyclopropyl | CF₃ | H | —SOCF₃ | H | H |
| CN | cyclopropyl | CF₃ | H | —SOCF₃ | H | Cl |
| CN | H | Cl | H | —OCF₂CHFCl | H | H |
| CN | H | Cl | H | —OCF₂CHFCl | H | Cl |
| CN | H | Br | H | —OCF₂CHFCl | H | H |
| CN | H | Cl | H | —OCF₂CHFCl | H | Br |
| CN | CH₃ | Cl | H | —OCF₂CHFCl | H | H |
| CN | CH₃ | Cl | H | —OCF₂CHFCl | H | Cl |
| CN | CH₃ | Br | H | —OCF₂CHFCl | H | H |
| CN | CH₃ | Br | H | —OCF₂CHFCl | H | Br |
| CN | C₂H₅ | Cl | H | —OCF₂CHFCl | H | H |
| CN | C₂H₅ | Cl | H | —OCF₂CHFCl | H | Cl |
| CN | C₂H₅ | Br | H | —OCF₂CHFCl | H | H |
| CN | C₂H₅ | Br | H | —OCF₂CHFCl | H | Br |
| CN | cyclopropyl | Cl | H | —OCF₂CHFCl | H | H |
| CN | cyclopropyl | Cl | H | —OCF₂CHFCl | H | Cl |
| CN | cyclopropyl | Br | H | —OCF₂CHFCl | H | H |
| CN | cyclopropyl | Br | H | —OCF₂CHFCl | H | Br |
| CN | H | Cl | H | —OCF₂CHCl₂ | H | H |
| CN | H | Cl | H | —OCF₂CHCl₂ | H | Cl |
| CN | H | Br | H | —OCF₂CHCl₂ | H | H |
| CN | H | Br | H | —OCF₂CHCl₂ | H | Br |
| CN | CH₃ | Cl | H | —OCF₂CHCl₂ | H | H |
| CN | CH₃ | Cl | H | —OCF₂CHCl₂ | H | Cl |
| CN | CH₃ | Br | H | —OCF₂CHCl₂ | H | H |
| CN | CH₃ | Br | H | —OCF₂CHCl₂ | H | Br |
| CN | C₂H₅ | Cl | H | —OCF₂CHCl₂ | H | H |
| CN | C₂H₅ | Cl | H | —OCF₂CHCl₂ | H | Cl |
| CN | C₂H₅ | Br | H | —OCF₂CHCl₂ | H | H |
| CN | C₂H₅ | Br | H | —OCF₂CHCl₂ | H | Br |
| CN | cyclopropyl | Cl | H | —OCF₂CHCl₂ | H | H |
| CN | cyclopropyl | Cl | H | —OCF₂CHCl₂ | H | Cl |
| CN | cyclopropyl | Br | H | —OCF₂CHCl₂ | H | H |
| CN | cyclopropyl | Br | H | —OCF₂CHCl₂ | H | Br |
| CN | H | Cl | H | —OCF₂CHF₂ | H | H |
| CN | H | Cl | H | —OCF₂CHF₂ | H | Cl |
| CN | H | Br | H | —OCF₂CHF₂ | H | H |
| CN | H | Br | H | —OCF₂CHF₂ | H | Br |
| CN | CH₃ | Cl | H | —OCF₂CHF₂ | H | H |
| CN | CH₃ | Cl | H | —OCF₂CHF₂ | H | Cl |
| CN | CH₃ | Br | H | —OCF₂CHF₂ | H | H |
| CN | CH₃ | Br | H | —OCF₂CHF₂ | H | Br |
| CN | C₂H₅ | Cl | H | —OCF₂CHF₂ | H | H |
| CN | C₂H₅ | Cl | H | —OCF₂CHF₂ | H | Cl |
| CN | C₂H₅ | Br | H | —OCF₂CHF₂ | H | H |
| CN | C₂H₅ | Br | H | —OCF₂CHF₂ | H | Br |
| CN | cyclopropyl | Cl | H | —OCF₂CHF₂ | H | H |
| CN | cyclopropyl | Cl | H | —OCF₂CHF₂ | H | Cl |
| CN | cyclopropyl | Br | H | —OCF₂CHF₂ | H | H |
| CN | cyclopropyl | Br | H | —OCF₂CHF₂ | H | Br |
| CN | H | Cl | H | —SO₂CF₃ | H | H |
| CN | H | Cl | H | —SO₂CF₃ | H | Cl |
| CN | H | Br | H | —SO₂CF₃ | H | H |
| CN | H | Br | H | —SO₂CF₃ | H | Br |
| CN | H | CF₃ | H | —SO₂CF₃ | H | H |
| CN | CH₃ | CF₃ | H | —SO₂CH₃ | H | H |
| CN | C₂H₅ | Cl | H | —SO₂CF₃ | H | Cl |
| CN | C₂H₅ | Br | H | —SO₂CF₃ | H | H |
| CN | C₂H₅ | Br | H | —SO₂CF₃ | H | Br |
| CN | C₂H₅ | CF₃ | H | —SO₂CF₃ | H | H |
| CN | cyclopropyl | Cl | H | —SO₂CF₃ | H | H |
| CN | cyclopropyl | Cl | H | —SO₂CF₃ | H | Cl |
| CN | cyclopropyl | Br | H | —SO₂CF₃ | H | H |

TABLE 1-continued

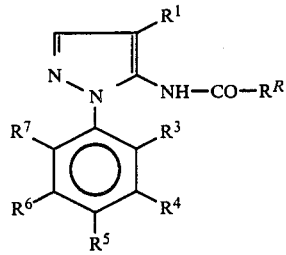

(I)

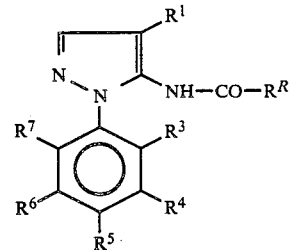

| R¹ | R² | R³ | R⁴ | R⁵ | R⁶ | R⁷ |
|---|---|---|---|---|---|---|
| CN | ▷—H | Br | H | —SO₂CF₃ | H | Br |
| CN | ▷—H | CF₃ | H | —SO₂CF₃ | H | H |
| CN | H | F | H | —SCCl₂F | H | H |
| CN | H | F | H | —SCCl₂F | H | F |
| CN | H | F | F | —SCCl₂F | F | F |
| CN | H | Cl | H | —SCCl₂F | H | H |
| CN | H | Cl | H | —SCCl₂F | H | Cl |
| CN | H | Cl | H | —SCCl₂F | H | F |
| CN | H | Br | H | —SCCl₂F | H | H |
| CN | H | Br | H | —SCCl₂F | H | Br |
| CN | CH₃ | F | H | —SCCl₂F | H | H |
| CN | CH₃ | F | H | —SCCl₂F | H | F |
| CN | CH₃ | F | F | —SCCl₂F | F | F |
| CN | CH₃ | Cl | H | —SCCl₂F | H | H |
| CN | CH₃ | Cl | H | —SCCl₂F | H | Cl |
| CN | CH₃ | Cl | H | —SCCl₂F | H | F |
| CN | CH₃ | Br | H | —SCCl₂F | H | H |
| CN | CH₃ | Br | H | —SCCl₂F | H | Br |
| CN | C₂H₅ | F | H | —SCCl₂F | H | H |
| CH | C₂H₅ | F | H | —SCCl₂F | H | F |
| CN | C₂H₅ | F | F | —SCCl₂F | F | F |
| CN | C₂H₅ | Cl | H | —SCCl₂F | H | H |
| CN | C₂H₅ | Cl | H | —SCCl₂F | H | Cl |
| CN | C₂H₅ | Cl | H | —SCCl₂F | H | F |
| CN | C₂H₅ | Br | H | —SCCl₂F | H | H |
| CN | C₂H₅ | Br | H | —SCCl₂F | H | Br |
| CN | ▷—H | F | H | —SCCl₂F | H | H |
| CN | ▷—H | F | H | —SCCl₂F | H | F |
| CN | ▷—H | F | F | —SCCl₂F | F | F |
| CN | ▷—H | Cl | H | —SCCl₂F | H | H |
| CN | ▷—H | Cl | H | —SCCl₂F | H | Cl |
| CN | ▷—H | Cl | H | —SCCl₂F | H | F |
| CN | ▷—H | Br | H | —SCCl₂F | H | H |
| CN | ▷—H | Br | H | —SCCl₂F | H | Br |
| CN | H | F | H | —OCHF₂ | H | H |
| CN | H | F | H | —OCHF₂ | H | F |
| CN | H | F | F | —OCHF₂ | F | F |
| CN | H | Cl | H | —OCHF₂ | H | H |
| CN | H | Cl | H | —OCHF₂ | H | Cl |
| CN | H | Cl | H | —OCHF₂ | H | F |
| CN | H | Br | H | —OCHF₂ | H | H |
| CN | H | Br | H | —OCHF₂ | H | Br |
| CN | CH₃ | F | H | —OCHF₂ | H | H |
| CN | CH₃ | F | H | —OCHF₂ | H | F |
| CN | CH₃ | F | F | —OCHF₂ | F | F |
| CN | CH₃ | Cl | H | —OCHF₂ | H | H |
| CN | CH₃ | Cl | H | —OCHF₂ | H | Cl |
| CN | CH₃ | Cl | H | —OCHF₂ | H | F |
| CN | CH₃ | Br | H | —OCHF₂ | H | H |
| CN | CH₃ | Br | H | —OCHF₂ | H | Br |
| CN | C₂H₅ | F | H | —OCHF₂ | H | H |
| CN | C₂H₅ | F | H | —OCHF₂ | H | F |
| CN | C₂H₅ | F | F | —OCHF₂ | F | F |
| CN | C₂H₅ | Cl | H | —OCHF₂ | H | H |
| CN | C₂H₅ | Cl | H | —OCHF₂ | H | Cl |
| CN | C₂H₅ | Cl | H | —OCHF₂ | H | F |
| CN | C₂H₅ | Br | H | —OCHF₂ | H | H |
| CN | C₂H₅ | Br | H | —OCHF₂ | H | Br |
| CN | ▷—H | F | H | —OCHF₂ | H | H |
| CN | ▷—H | F | H | —OCHF₂ | H | F |
| CN | ▷—H | F | F | —OCHF₂ | F | F |
| CN | ▷—H | Cl | H | —OCHF₂ | H | H |
| CN | ▷—H | Cl | H | —OCHF₂ | H | Cl |
| CN | ▷—H | Cl | H | —OCH₂F | H | F |
| CN | ▷—H | Br | H | —OCHF₂ | H | H |
| CN | ▷—H | Br | H | —OCHF₂ | H | Br |
| CN | Cl-▷-Cl (CH₃) | Cl | H | —OCF₃ | H | H |
| CN | Cl-▷-Cl (CH₃) | Cl | H | —OCF₃ | H | Cl |

TABLE 1-continued

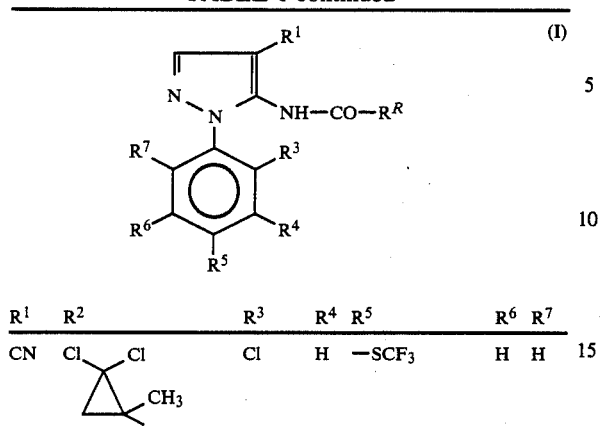

| R¹ | R² | R³ | R⁴ | R⁵ | R⁶ | R⁷ |
|---|---|---|---|---|---|---|
| CN | 1,1-dichloro-2-methylcyclopropyl | Cl | H | —SCF₃ | H | H |
| CN | 1,1-dichloro-2-methylcyclopropyl | Cl | H | —SCF₃ | H | Cl |
| CN | 1,1-dichloro-2-methylcyclopropyl | Cl | H | —SO₂CF₃ | H | H |
| CN | 1,1-dichloro-2-methylcyclopropyl | Cl | H | —SO₂CF₃ | H | Cl |
| CN | phenyl | Cl | H | —OCF₃ | H | Cl |
| CN | phenyl | Cl | H | —SCF₃ | H | Cl |
| CN | 4-chlorophenyl | Cl | H | —OCF₃ | H | Cl |
| CN | 4-chlorophenyl | Cl | H | —SCF₃ | H | Cl |
| CN | 4-methylphenyl | Cl | H | —OCF₃ | H | Cl |
| CN | 4-methylphenyl | Cl | H | —SCF₃ | H | Cl |
| CN | 4-nitrophenyl | Cl | H | —OCF₃ | H | Cl |

TABLE 1-continued

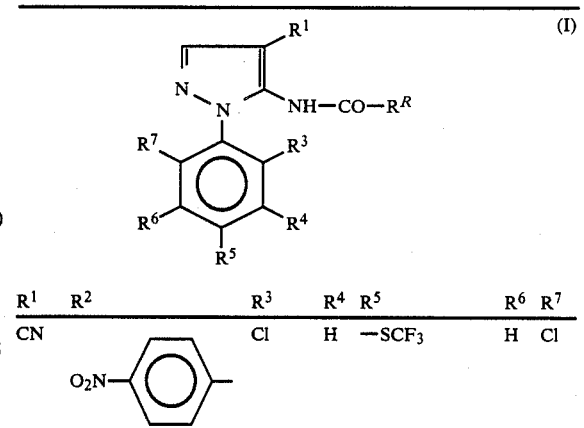

| R¹ | R² | R³ | R⁴ | R⁵ | R⁶ | R⁷ |
|---|---|---|---|---|---|---|
| CN | 4-nitrophenyl | Cl | H | —SCF₃ | H | Cl |

If, for example, 5-amino-4-cyano-1-(2',6'-dichloro-4'-trifluoromethylthio-phenyl)-pyrazole and proionyl chloride are used as starting substances, the course of the reaction in the process according to the invention can be represented by the following equation:

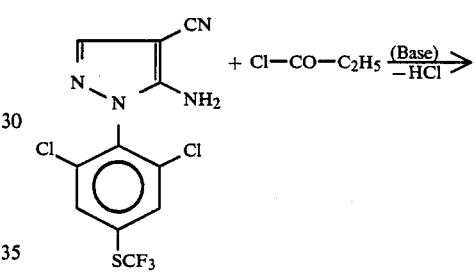

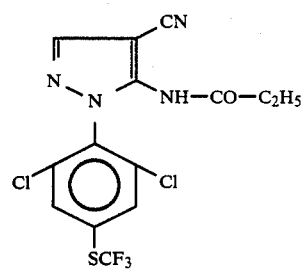

Formula (II) provides a general definition of the 5-aminopyrazoles required as starting substances for carrying out the process according to the invention. In this formula (II), R¹, R³, R⁴, R⁵, R⁶ and R⁷ preferably have those meanings which have already been mentioned as preferred for these substituents in the description of the substances of the formula (I) according to the invention.

Some of the 5-aminopyrazoles of the formula (II) are known (compare, for example, European No. 34,945; DE-OS (German Published Specification) No. 3,226,496 and DE-OS (German Published Specification) No. 3,129,429).

5-Aminopyrazoles of the formula (IIa)

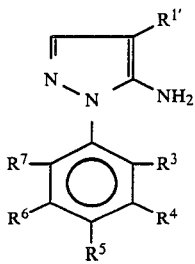
(IIa)

in which $R^{1'}$ represents alkoxycarbonyl, alkenyloxycarbonyl, alkinyloxycarbonyl, alkenylaminocarbonyl or alkinylaminocarbonyl and $R^3$, $R^4$, $R^5$, $R^6$ and $R^7$ have the abovementioned meaning, are not yet known.

However, these compounds are obtained by processes which are known in principle, in which acrylonitrile derivatives of the formula (IVa)

(IVa)

in which $R^{1'}$ has the abovementioned meaning, are reacted with phenylhydrazines of the formula (V)

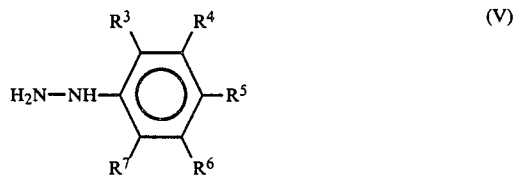
(V)

in which $R^3$, $R^4$, $R^5$, $R^6$ and $R^7$ have the abovementioned meaning, either initially in a first stage, if appropriate in the presence of a diluent, such as, for example, glacial acetic acid or ethanol, and if appropriate in the presence of a reaction assistant, such as, for example, sodium acetate, at temperatures between −20° C. and +20° C., to give the phenylhydrazine derivatives of the formula (VIa)

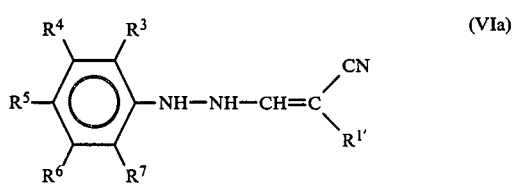
(VIa)

in which $R^{1'}$, $R^3$, $R^4$, $R^5$, $R^6$ and $R^7$ have the abovementioned meaning, and these are cyclized in a second stage, if appropriate in the presence of a diluent, such as, for example, ethylene glycol monoethyl ether, at temperatures between +50° C. and +150° C., or the compounds of the formulae (VIa) are directly cyclized in one reaction step, without isolation of the intermediate stage of the (VIa), if appropriate in the presence of a diluent, such as, for example, ethylene glycol monoethyl ether or ethanol, at temperatures between +50° C. and +150° C.

5-Aminopyrazoles of the formula (IIb)

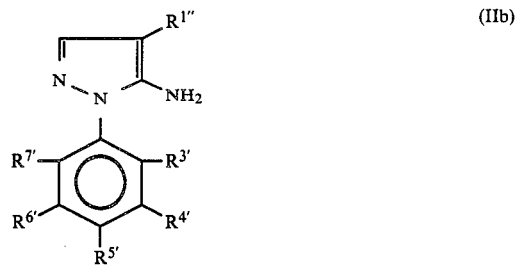
(IIb)

in which $R^{1''}$ represents cyano or alkylaminocarbonyl and $R^{3'}$, $R^{4'}$, $R^{5'}$, $R^{6'}$ and $R^{7'}$, which are identical or different, represent hydrogen, halogen, cyano, nitro, alkyl, alkoxy, alkylsulphonyl, alkoxycarbonyl or the radical —X—$R^8$, wherein X represents oxygen, sulphur, sulphinyl or sulphonyl and $R^8$ represents halogenoalkyl, with the proviso that at least one of the radicals $R^{3'}$, $R^{4'}$, $R^{5'}$, $R^{6'}$ or $R^{7'}$ represents a radical —X—$R^8$, and X does not represent oxygen if $R^8$ represents trifluoromethyl, are also not yet known.

They are likewise obtained in an analogous manner to the 5-aminopyrazoles of the formula (IIa) by processes which are known in principle, in which acrylonitrile derivatives of the formula (IVb)

(IVb)

in which $R^{1''}$ has the abovementioned meaning, are reacted with phenylhydrazines of the formula (Va)

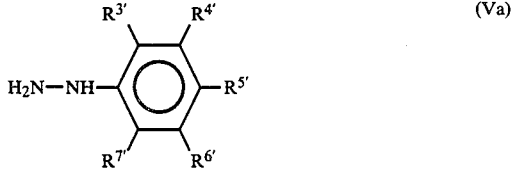
(Va)

in which $R^{3'}$, $R^{4'}$, $R^{5'}$, $R^{6'}$ and $R^{7'}$ have the abovementioned meaning, either initially in a first stage, if appropriate in the presence of a diluent, such as, for example, glacial acetic acid or ethanol, and if appropriate in the presence of a reaction assistant, such as, for example, sodium acetate, at temperatures between −20° C. and +20° C., to give the phenylhydrazine derivatives of the formula (VIb)

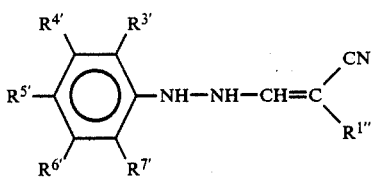

(VIb)

in which

R[1"], R[3'], R[4'], R[5'], R[6'] and R[7'] have the abovementioned meaning, and these are cyclized in a 2nd stage, if appropriate in the presence of a diluent, such as, for example, ethylene glycol monoethyl ether, at temperatures between $+50°$ C. and $+150°$ C., or the compounds of the formulae (Ivb) and (Va) are directly cyclized in one reaction step, without isolation of the intermediate stage of the formula (VIb), if appropriate in the presence of a diluent, such as, for example, ethylene glycol monomethyl ether or ethanol, at temperatures between $+50°$ C. and $+150°$ C.

The acrylonitrile derivatives of the formulae (Iva) and (Ivb) are known (compare, for example, European No. 34,945 or DE-OS (German Published Specification) No. 3,129,429).

The phenylhydrazines of the formulae (V) and (Va) are known in most cases, or they can be prepared in a simple manner by processes analogous to known processes (compare, for example, Houben-Weyl, "Methoden der organischen Chemie" ("Methods of Organic Chemistry"), Volume X/2, page 203, Thieme Verlag Stuttgart 1967), for example by reacting the known anilines of the formula (VII)

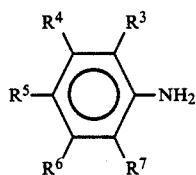

(VII)

in which

R[3], R[4], R[5], R[6] or R[7] have the abovementioned meaning, with sodium nitrite in the presence of an acid, such as, for example, sulphuric acid, and then with tin-II chloride, likewise in the presence of an acid, such as, for example, hydrochloric acid, at temperatures between $-20°$ C. and $+80°$ C.

Formula (III) provides a general definition of the acylating agents also required as starting substances for carrying out the process according to the invention. In this formula (III), R[2] preferably has those meanings which have already been mentioned as preferred for these radicals in the description of the substances of the formula (I) according to the invention. A preferably represents halogen, in particular chlorine or bromine, or a radical R[2]—CO—O—, R[2] having the abovementioned meaning. The acylating agents of the formula (III) are generally known compounds of organic chemistry.

Possible diluents for carrying out the process according to the invention are inert organic solvents. Preferred solvents which are used are aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether or diisopropyl ether, ethylene glycol dimethyl ether, tetrahydrofuran or dioxane, ketones, such as acetone or butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric acid triamide.

If acylating agents of the formula (III) are used in liquid form, it is also possible to employ these in an appropriate excess as the diluent.

Possible acid-binding agents for the process according to the invention are all the inorganic and organic bases which can usually be employed. Bases which are preferably used are alkali metal hydroxides or carbonates, such as, for example, sodium hydroxide, potassium hydroxide, sodium carbonate or potassium carbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in the process according to the invention. In general, the reaction is carried out between $-20°$ C. and $+150°$ C., preferably between $0°$ C. and $+100°$ C.

For carrying out the process according to the invention, in general 1 to 20 moles, preferably 1 to 15 moles, of acylating agent of the formula (III) and in general 1 to 3 moles, preferably 1 to 2 moles, of acid-binding agent are employed per mole of 5-aminopyrazole of the formula (II). The reaction procedure, working up and isolation of the end products of the formula (I) are effected in the customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Besides a particularly good general herbicidal activity, the active compounds of the formula (I) thereby also show a considerably improved crop plant selectivity in important crops.

The intermediates of the formula (II) and the intermediates of the formulae (VIa) and (VIb) likewise have herbicidal actions and a pronounced selectivity towards important crop plants.

When applied in appropriate amounts, the active compounds of the formula (I) according to the invention and their intermediates of the formula (II) also have a fungicidal action, for example against the rice disease pathogen Pyricularia oryzae.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components of the mixtures are known herbicides, for example diphenyl ether, pyridoxy-phenoxypropionic acids, phenoxyalkanecarboxylic acids, ureas, triazinones or triazindiones, such as, for example, 2-benzyloxyethyl, 2,2-diethoxyethyl or trimethylsilylmethyl α-[4-(3,5-dichloro-2-pyridoxy)-phenoxy]-propionate, 2,4-dichlorophenoxyacetic acid, α-(2,4-dichlorophenoxy)-propionic acid, 4-chloro-2-methylphenoxyacetic acid, α-(4-chloro-2-methylphenoxy)-propionic acid, 1-amino-6-ethylthio-3-(2,2-dimethylpropyl)-1,3,5-triazine-2,4(1H,3H)dione or N-(2-benzothiazolyl)-N,N'-dimethyl-urea, for combating weeds in cereals; 4-amino-3-methyl-6-phenyl-1,2,4-triazin-5(4H)-one, for combating weeds in sugar beet; and 4-amino-6-(1,1-dimethylethyl)-3-methylthio- or -3-ethylthio-1,2,4-triazin-5(4H)-one, for combating weeds in soya bean. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and the use of the active compounds according to the invention can be seen from the following examples.

PREPARATION EXAMPLES

Example 1

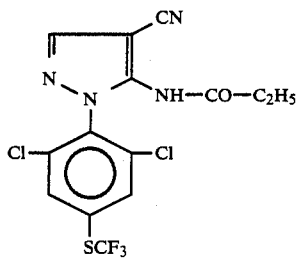

First 10 ml (0.11 mole) of propionyl chloride and then 1.8 ml (0.02 mole) of pyridine in 15 ml of chloroform are added to a suspension of 3.5 g (0.01 mole) of 5-amino-4-cyano-1-(2,6-dichloro-4-trifluoromethylthio-phenyl)-pyrazole in 30 ml of chloroform at 0° C., with stirring. A clear solution is obtained, and, when the addition has ended, stirring is continued at room temperature for 20 hours. The solution thus obtained is evaporated to dryness. For working up, the residue is taken up in 50 ml of ethanol, aqueous ammonia is added until the reaction is alkaline, the mixture is heated under reflux for 10 minutes, the volatile constituents are removed in vacuo, the residue is taken up in 100 ml of chloroform, the mixture is washed with water, then with 2N aqueous hydrochloric acid and again with water and dried over sodium sulphate and the solvent is removed in vacuo. 3.4 g (83% of theory) of 5-propionylamino-4-cyano-1-(2,6-dichloro-4-trifluoromethylthio-phenyl)-pyrazole of melting point 153° C. to 156° C. are obtained.

Example 2

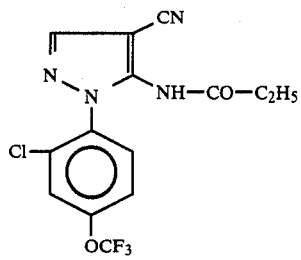

10 ml (0.11 mole) of propionyl chloride are added to 2.9 g (0.01 mole) of 5-amino-4-cyano-1-(2-chloro-4-trifluoromethoxy-phenyl)-pyrazole in 30 ml of chloroform at 0° C., with stirring, and a solution of 1.8 ml (0.02 mole) of pyridine in 15 ml of chloroform is then added, also at 0° C. When the addition has ended, stirring is continued at room temperature for 20 hours, the solvent is stripped off, the residue is taken up in 50 ml of ethanol, aqueous ammonia is added until the reaction is alkaline, the volatile constituents are removed in vacuo, the residue is taken up in 100 ml of chloroform, the mixture is washed with water, then with 2N aqueous hydrochloric acid and again with water and dried over sodium sulphate and the solvent is removed in vacuo. 2.7 g (75.3% of theory) of 4-cyano-1-(2-chloro-4-trifluoromethoxy-phenyl)-5-propionylamino-pyrazole of melting point 127° C. are obtained.

The following compounds of the general formula (I) are obtained in a corresponding manner, according to the general preparation disclosure:

TABLE 2

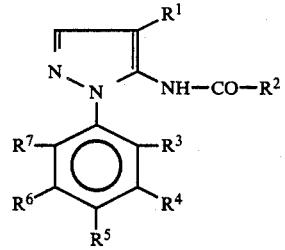

(I)

| Example No. | $R^1$ | $R^2$ | $R^3$ | $R^4$ | $R^5$ | $R^6$ | $R^7$ | Melting point (°C.) |
|---|---|---|---|---|---|---|---|---|
| 3 | $C_2H_5OCO-$ | $C_2H_5$ | Cl | H | $CF_3$ | H | Cl | 63–67 |
| 4 | $C_2H_5OCO-$ | $C_2H_5$ | Cl | H | $CF_3$ | H | H | 87–89 |
| 5 | CN | $C_2H_5$ | H | Cl | $OCF_3$ | H | H | 142–143 |
| 6 | CN | $C_2H_5$ | H | H | $OCF_3$ | H | H | 152–153 |
| 7 | $C_2H_5OCO-$ | $C_2H_5$ | Cl | H | $OCF_3$ | H | Cl | 84–85 |
| 8 | $C_2H_5OCO-$ | $C_2H_5$ | Cl | H | $OCF_3$ | H | H | oil $n_D^{20} = 1,507$ |
| 9 | CN | $C_2H_5$ | H | H | $SCF_3$ | H | H | 171 |
| 10 | CN | $C_2H_5$ | H | Cl | $SCF_3$ | H | H | 143 |
| 11 | CN | $C_2H_5$ | Cl | H | $SCF_3$ | H | H | 161–163 |
| 12 | CN | $CH_3$ | Cl | H | $SCF_3$ | H | Cl | 173–175 |
| 13 | $C_2H_5OCO-$ | $C_2H_5$ | H | Cl | $SCF_3$ | H | H | 136–137 |
| 14 | CN | $C_2H_5$ | $CF_3$ | H | $CF_3$ | H | H | 150–154 |
| 15 | CN | $C_2H_5$ | $CF_3$ | H | $F_3C-SO_2-$ | H | H | 188–190 |
| 16 | CN | $C_2H_5$ | Cl | H | $F_3C-SO_2-$ | H | H | 160 |
| 17 | CN | $C_2H_5$ | H | $CF_3$ | Cl | H | H | 186 |
| 18 | CN | $C_2H_5$ | $CF_3$ | H | $CH_3-SO_2-$ | H | H | 148 |
| 19 | CN | $C_2H_5$ | $CF_3$ | H | $CH_3-SO_2-$ | H | Cl | 198 |
| 20 | CN | $C_2H_5$ | Cl | H | $F_3C-SO_2-$ | H | Cl | 197 |
| 21 | CN | $Cl-CH_2$ | Cl | H | $F_3CS-$ | H | Cl | 79 |
| 22 | CN | $C_2H_5$ | H | H | $ClF_2C-SO_2-$ | H | Cl | 213–214 |

TABLE 2-continued

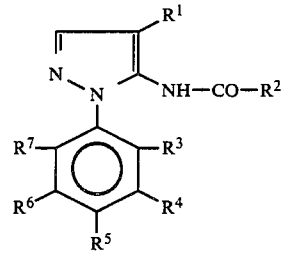

(I)

| Example No. | R¹ | R² | R³ | R⁴ | R⁵ | R⁶ | R⁷ | Melting point (°C.) |
|---|---|---|---|---|---|---|---|---|
| 23 | H₂N—CO— | C₂H₅ | Cl | H | F₃C—S— | H | Cl | 170–171 |
| 24 | CN | C₂H₅ | CF₃ | H | H | H | CF₃ | 205 |
| 25 | CN | cyclopropyl-H | Cl | H | F₃C—S— | H | Cl | 209 |
| 26 | CN | Cl—CH₂— | Cl | H | F₃C—O— | H | H | 125–128 |
| 27 | CN | cyclopropyl-H | Cl | H | F₃C—O— | H | H | 116 |
| 28 | CN | n-C₃H₇ | Cl | H | F₃C—O— | H | H | 111 |
| 29 | CN | (CH₃)₂CH—CH₂— | Cl | H | F₃C—O— | H | H | 95–98 |
| 30 | CN | Cl—CH₂—CH₂— | Cl | H | F₃C—O— | H | H | 109 |
| 31 | CN | Br—C(CH₃)₂— | Cl | H | F₃C—O— | H | H | 120 |
| 32 | CN | (CH₃)₃C— | Cl | H | F₃C—O— | H | H | 159 |
| 33 | CN | CH₃—(CH₂)₁₀— | Cl | H | F₃C—O— | H | H | 70–72 |
| 34 | CN | CH₃—(CH₂)₃— | Cl | H | F₃C—O— | H | H | 84–87 |
| 35 | CN | CH₃ | Cl | H | F₃C—O— | H | H | 145–146 |
| 36 | CN | C₂H₅—CH(CH₃)— | Cl | H | F₃C—O— | H | H | 107–109 |
| 37 | CN | CH₃ | Cl | H | F₃C—O— | H | Cl | 181–182 |
| 38 | CN | C₂H₅ | Cl | H | F₃C—O— | H | Cl | |
| 39 | CN | (CH₃)₂CH— | Cl | H | F₃C—O— | H | H | 125–129 |
| 40 | CN | CH₃O—CH₂— | Cl | H | F₃C—O— | H | H | 102 |
| 41 | CN | CH₃S—CH₂— | Cl | H | F₃C—S— | H | Cl | 132–135 |
| 42 | CN | CH₃O—CH₂— | Cl | H | F₃C—S— | H | Cl | 158–160 |
| 43 | CN | CH₃S—CH₂— | Cl | H | F₃C—O— | H | H | 115 |

Preparation of the starting substances

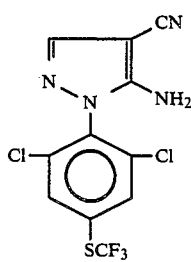

(II-1)

14.1 g (0.04 mole) of 1-(2,2-dicyanethen-1-yl)-2-(2,6-dichloro-4-trifluoromethylthio-phenyl)-hydrazine in 30 ml of ethylene glycol monoethyl ether are heated under reflux for 2 hours. Active charcoal is added to the hot solution, the mixture is filtered and the filtrate is diluted with 60 ml of water. The precipitate which has separated out is filtered off with suction and dried. 9.8 g (70% of theory) of 5-amino-4-cyano-1-(2,6-dichloro-4-trifluoromethylthio-phenyl)-pyrazole of melting point 185° C. to 187° C. are obtained.

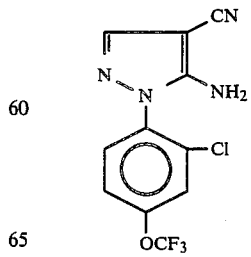

(II-2)

3.08 g (0.025 mole) of ethoxymethylenemalonic acid dinitrile and 5.7 g (0.025 mole) of 2-chloro-4-trifluoromethoxy-phenylhydrazine in 50 ml of ethylene glycol monoethyl ether are heated under reflux for 3 hours and, after the mixture has been cooled, it is poured onto water, the crystalline precipitate is filtered off with suction and stirred with petroleum ether, the mixture is cooled and the precipitate is filtered off again with suction. 5.3 g (73.6% of theory) of 5-amino-4-cyano-1-(2-chloro-4-trifluoromethoxyphenyl)-pyrazole of melting point 115° C. are obtained.

The following new 5-aminopyrazoles of the formula (II) are obtained in a corresponding manner according to the general preparation statements:

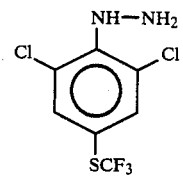
(V-1)

16.6 g (0.24 mole) of sodium nitrite in 150 ml of concentrated sulphuric acid are first added to 50 g (0.2 mole) of 2,6-dichloro-4-trifluoromethylthio-aniline in

TABLE 3

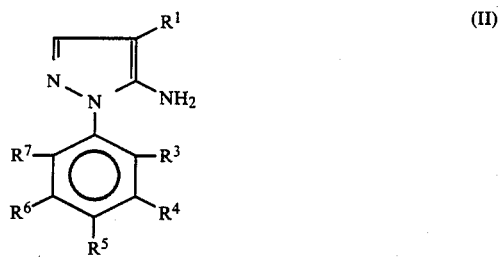
(II)

| Example No. | $R^1$ | $R^3$ | $R^4$ | $R^5$ | $R^6$ | $R^7$ | Melting point (°C.) |
|---|---|---|---|---|---|---|---|
| II-3 | $C_2H_5OCO-$ | Cl | H | $CF_3$ | H | Cl | 134–35 |
| II-4 | $C_2H_5OCO-$ | Cl | H | $CF_3$ | H | H | 112–114 |
| II-5 | $C_2H_5OCO-$ | Cl | H | $OCF_3$ | H | H | 115–118 |
| II-6 | $C_2H_5OCO-$ | Cl | H | $OCF_3$ | H | Cl | 153–154 |
| II-7 | CN | Cl | H | $SCF_3$ | H | H | 159 |
| II-8 | CN | H | Cl | $SCF_3$ | H | H | 126–128 |
| II-9 | CN | H | H | $SCF_3$ | H | H | 122 |
| II-10 | $C_2H_5OCO-$ | H | Cl | $SCF_3$ | H | H | 120–122 |
| II-11 | $C_2H_5OCO-$ | Cl | H | $SCF_3$ | H | H | 129–130 |
| II-12 | CN | $CF_3$ | H | $CF_3$ | H | H | 173 |
| II-13 | CN | $CF_3$ | H | $CH_3-SO_2-$ | H |  | 188–191 |
| II-14 | CN | $CF_3$ | H | $F_3C-SO_2-$ | H | H | 174–176 |
| II-15 | CN | H | $CF_3$ | Cl | H | H | 118 |
| II-16 | CN | Cl | H | $F_3C-SO_2-$ | H | H | 187–189 |
| II-17 | CN | $CF_3$ | H | $CH_3-SO_2-$ | H | Cl | 181 |
| II-18 | CN | Cl | H | $F_3C-SO_2-$ | H | Cl | 254 |
| II-19 | CN | Cl | H | $ClF_2C-SO_2-$ | H | Cl | 211 |
| II-20 | CN | $CF_3$ | H | H | H | $CF_3$ | 200–203 |
| II-21 | CN | Cl | H | $F_3C-O-$ | H | Cl | 171 |

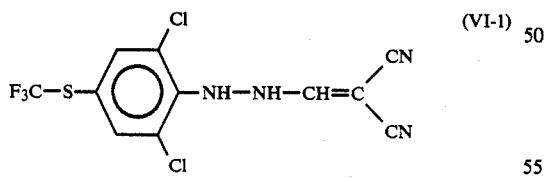
(VI-1)

6.1 g (0.05 mole) of ethoxymethylenemalonic acid dinitrile are added to a suspension of 13.9 g (0.05 mole) of (2,6-dichloro-4-trifluoromethylthio)-phenylhydrazine and 2.1 g (0.025 mole) of sodium acetate in 25 ml of glacial acetic acid, with stirring. When the addition has ended, stirring is continued at room temperature for one hour and the solid thus obtained is filtered off, washed successively with water, aqueous sodium bicarbonate solution and again with water and then dried. 15.8 g (89% of theory) of 1-(2,2-dicyanethen-1-yl)-2-(2,6-dichloro-4-trifluoromethylthiophenyl)-hydrazine of melting point 160° C. are obtained.

435 ml of glacial acetic acid at 55° C. to 60° C., and 180.5 g (0.8 mole) of tin-II chloride dihydrate in 188 ml of concentrated hydrochloric acid are then added at 5° C. to 10° C. The precipitate thus obtained is filtered off with suction, stirred in 650 ml of a mixture of ice and aqueous ammonia solution, filtered off with suction, dried and boiled up twice with in each case one liter of chloroform, the mixture is filtered and the filtrate is freed from the solvent in vacuo. 33 g (62.4% of theory) of (2,6-dichloro-4-trifluoromethylthio)-phenylhydrazine of melting point 58° C. are obtained.

The following new intermediates of the formula (V) are obtained in a corresponding manner according to the general preparation statements:

TABLE 4

(V)

R⁴, R³ on benzene ring with R⁵, R⁶, R⁷ and —NH—NH₂ substituent

| Example No. | R³ | R⁴ | R⁵ | R⁶ | R⁷ | Melting point (°C.) |
|---|---|---|---|---|---|---|
| V-2 | Cl | H | OCF₃ | H | H | 35 |
| V-3 | Cl | H | OCF₃ | H | Cl | 61 |
| V-4 | H | Cl | OCF₃ | H | H | 41–42 |
| V-5 | H | H | OCF₃ | H | H | Oil, $n_D^{20} = 1.4799$ |
| V-6 | H | H | SCF₃ | H | H | 55 |
| V-7 | H | Cl | SCF₃ | H | H | 72 |
| V-8 | Cl | H | SCF₃ | H | H | 83 |

Use Examples

The compound shown below is used as the comparison substance in the use examples which follow:

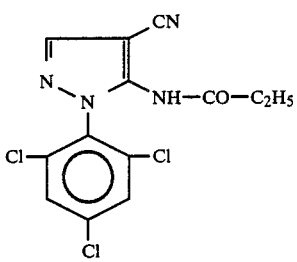

(A)

4-Cyano-5-propionylamino-1-(2,4,6-trichlorophenyl)-pyrazole (known from DE-OS (German Published Specification) No. 3,226,513).

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this Example, for example, the compound according to preparation example (1) exhibits a clear superiority in herbicidal activity and also in selectivity in useful plants compared with the prior art; this particularly applies to wheat.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this example, for example, the compound according to preparation Example (1) exhibits a clear superiority in herbicidal activity and also in selectivity in useful plants compared with the prior art. This particularly applies to wheat.

It will be understood that the specification and examples are illustrative but not limitative of the present invention and that other embodiments within the spirit and scope of the invention will suggest themselves to those skilled in the art.

We claim:

1. A 5-aminopyrazole of the formula

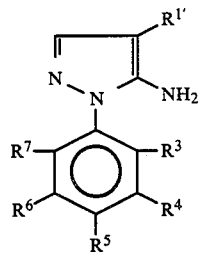

in which
R¹' represents alkenylaminocarbonyl or alkinylaminocarbonyl with in each case up to 4 carbon atoms is the individual hydrocarbyl parts and R³, R⁴, R⁵, R⁶ and R⁷, which are identical or different, represent hydrogen, halogen, cyano, nitro, alkyl, alkoxy, alkylsulphonyl, alkoxycarbonyl with up to 4 carbon atoms in the particular alkyl parts or a radical —(X)ₙ—R⁸, wherein X represents oxygen, sulphur, sulphinyl or sulphonyl, n represent 0 or 1 and R⁸ represents halogenoalkyl with up to 4 carbon atoms and up to 9 halogen atoms, with the proviso that at least one of the radicals R³, R⁴, R⁵, R⁶ or R⁷ represents a radical —(X)ₙ—R⁸ and when R¹' is methoxycarbonyl R³ cannot be trifluoromethyl and R⁵ cannot be chloro.

2. An aminopyrazole of the formula

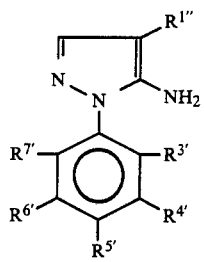

in which $R^{1''}$ represents cyano or alkylaminocarbonyl with up to 4 carbon atoms in the hydrocarbyl part and
$R^{3'}$, $R^{4'}$, $R^{5'}$, $R^{6'}$ and $R^{7'}$, which are identical or different, represent hydrogen, halogen, cyano, nitro, alkyl, alkoxy, alkylsulphonyl, alkoxycarbonyl with up to 4 carbon atoms in the particular alkyl parts or the radical —X—$R^8$, wherein X represents sulphur, sulphinyl or sulphonyl and
$R^8$ represents halogenalkyl with up to 4 carbon atoms and up to 9 halogen atoms, with the proviso that at least one of the radicals $R^{3'}$, $R^{4'}$, $R^{5'}$, $R^{6'}$ or $R^{7'}$ represents a radical —X—$R^8$.

* * * * *

UNITED STATES PATENT AND TRADEMARK OFFICE
CERTIFICATE OF CORRECTION

PATENT NO. : 4,791,212

DATED : Dec. 13, 1988

INVENTOR(S) : Gehring et al.

It is certified that error appears in the above-identified patent and that said Letters Patent is hereby corrected as shown below:

Col. 28, line 51    Delete "is" and substitute --in--

Signed and Sealed this

Twenty-eighth Day of November 1989

Attest:

JEFFREY M. SAMUELS

Attesting Officer    Acting Commissioner of Patents and Trademarks